United States Patent [19]

Kwak

[11] 4,284,832
[45] Aug. 18, 1981

[54] CONVERSION OF CS (TEAR GAS) TO O-CHLOROSTYRENE AND AMMONIUM SULFATE

[75] Inventor: Solim S. W. Kwak, Orem, Utah

[73] Assignee: The United States of America as represented by the Secretary of the Army, Washington, D.C.

[21] Appl. No.: 144,130

[22] Filed: Apr. 28, 1980

[51] Int. Cl.³ ............................................. C07C 25/00
[52] U.S. Cl. .................................. 570/190; 423/545; 423/549; 562/495
[58] Field of Search ................... 260/650 R; 423/549, 423/545; 562/495; 570/190

[56] References Cited

U.S. PATENT DOCUMENTS

| 2,824,144 | 2/1958 | Beets et al. | 260/650 R |
| 3,898,292 | 8/1975 | Diamond | 260/650 R |
| 3,912,784 | 10/1975 | Suzuki | 260/650 R |
| 4,012,454 | 3/1977 | Fields | 260/650 R |

FOREIGN PATENT DOCUMENTS

| 815163 | 6/1959 | United Kingdom | 423/545 |
| 399497 | 4/1974 | U.S.S.R. | 585/437 |

Primary Examiner—Delbert E. Gantz
Assistant Examiner—Joseph A. Boska
Attorney, Agent, or Firm—Nathan Edelberg; Robert P. Gibson; Robert O. Richardson

[57] ABSTRACT

Tear gas or CS (o-Chlorobenzalmalononitrile) has two nitrile functional groups which, when removed, effects the chemical conversion of bulk CS to o-chlorostyrene. This involves a first step, an acid or base catalyzed hydrolysis of CS to o-chlorocinnamic acid. Thereafter a second reaction is the decarboxylation of the intermediate product to give o-chlorostyrene.

CS is reacted with 70% sulfuric acid at 120° C., producing ammonium sulfate and orth-ochlorocinnamic acid (the intermediate product). This intermediate product is separated and thermally decarboxylated at 270° C. (with a catalytic amount of soda lime and copper powder) to ortho-chlorostyrene.

7 Claims, 7 Drawing Figures

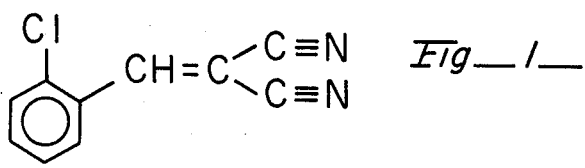
Fig—1—
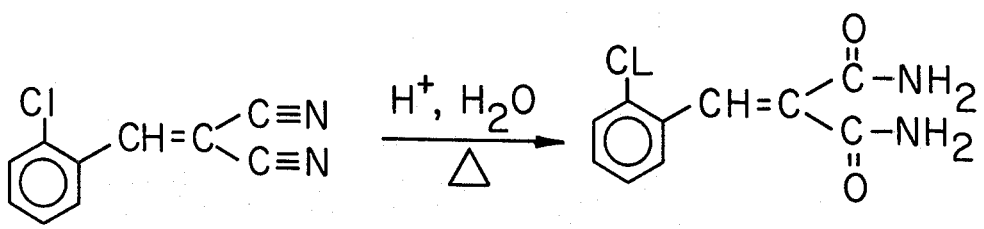
Fig—2—
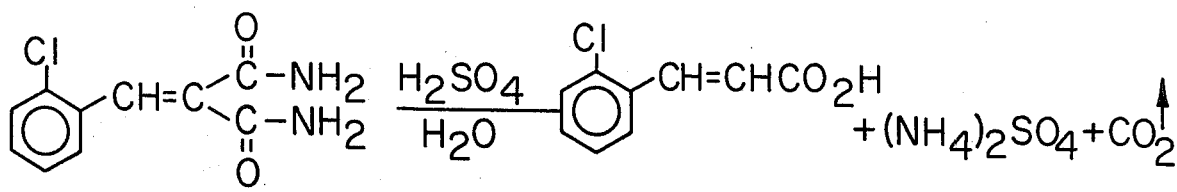
Fig—3—
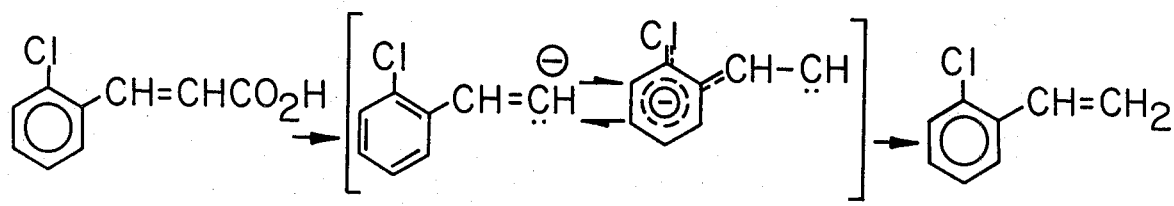
Fig—4—
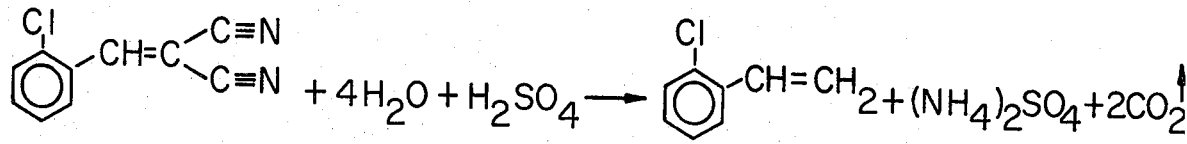
Fig—5—

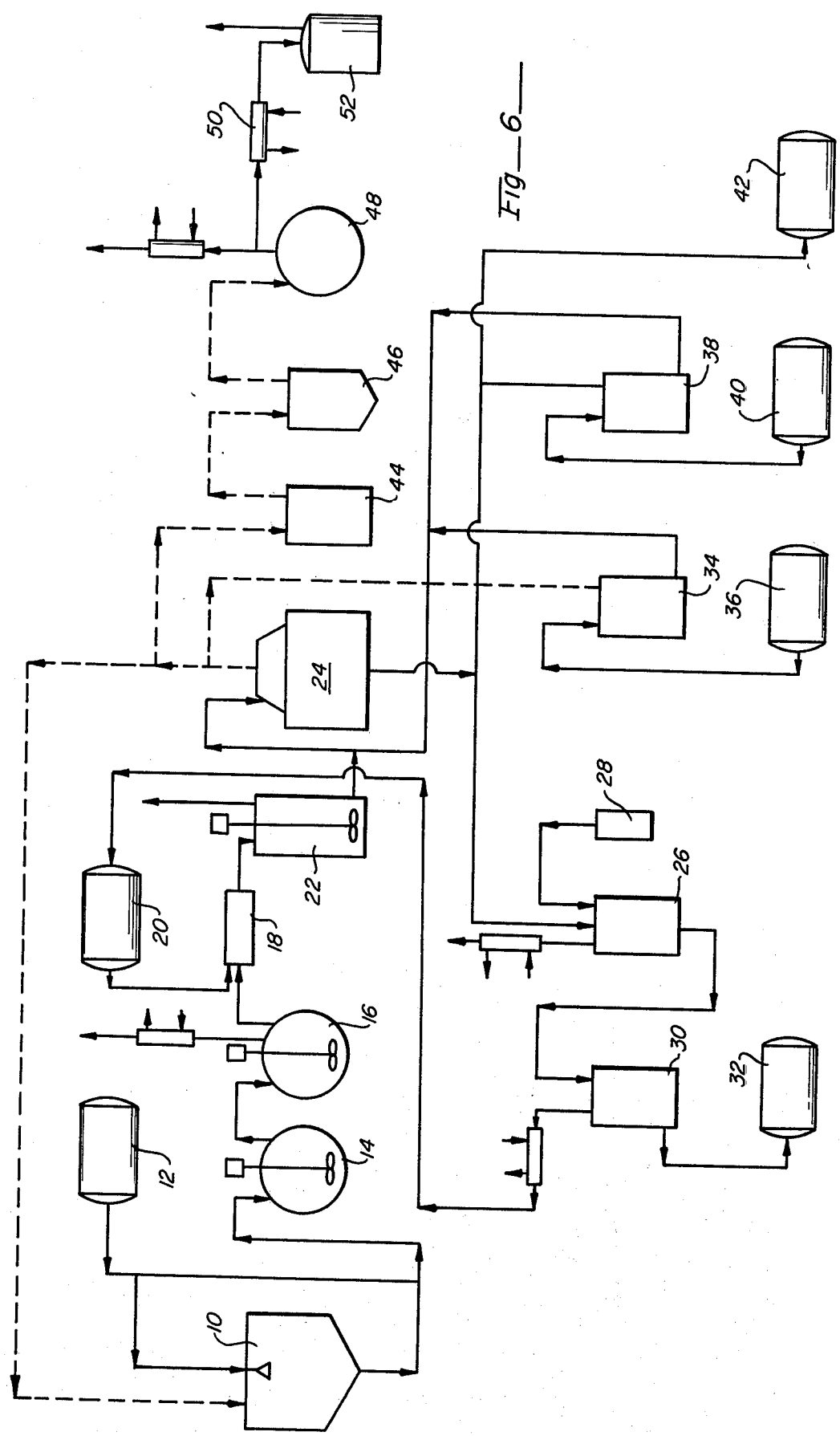
Fig_6

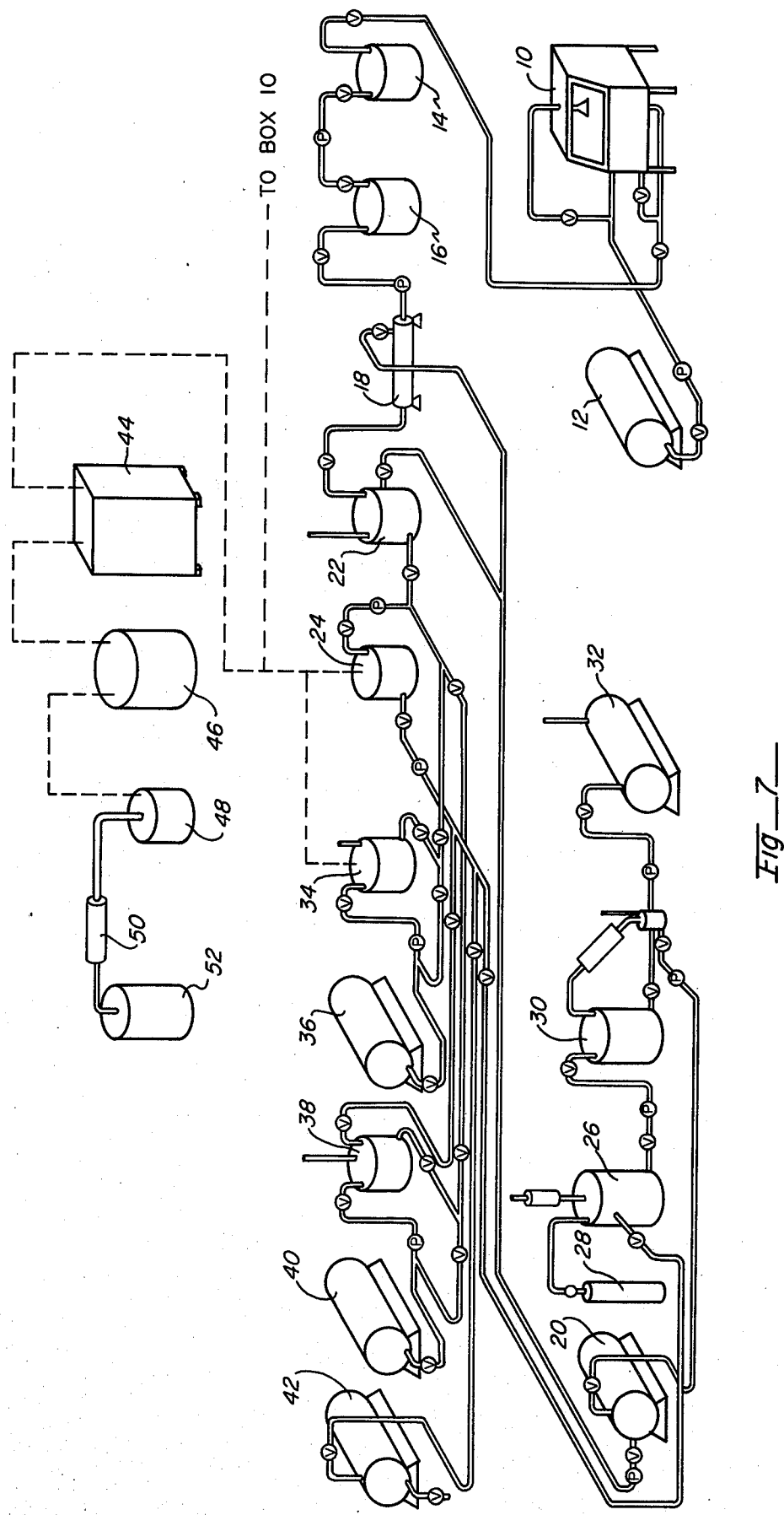
Fig_7

4,284,832

CONVERSION OF CS (TEAR GAS) TO O-CHLOROSTYRENE AND AMMONIUM SULFATE

GOVERNMENT RIGHTS

The invention described herein may be manufactured and/or used by or for the Government for governmental purposes without the payment of any royalty thereon.

BACKGROUND OF THE INVENTION

The disposal of surplus or waste chemicals is always a problem. Avoidance of contamination of the environment and pollution is a constant goal. A currently approved and planned method for the disposal of incapacitating chemical agents such as CS (tear gas) or ortho-chlorobenzalmalononitrile is burning it in multiple stage incinerators. This method not only results in the loss of a valuable raw material, but is also an expensive disposal process without any economic returns. Moreover, burning produces chlorinated hydrocarbons, condensed aromatic hydrocarbons and cyanide gas, all highly undesirable chemicals. When large quantities of CS are available for disposal, the most efficient, economical and environmentally acceptable disposal processes should be considered.

SUMMARY OF THE PRESENT INVENTION

In accordance with the present invention, an incapaciting material such as bulk CS or o-chlorobenzalmalononitrile is converted into a marketable non-toxic raw material, o-chlorostyrene, and a salable by-product, ammonium sulfate.

CS is a white to cream colered powder that smells like pepper and is used as a riot control or tearing agent, which is incorporated into candles, grenades, and mechanical containers for dispersing. It is stable at room temperature and boils at 310°–315° C., and causes, upon exposure to the body, tearing, skin irritation, and vomiting. It may also cause a temporary pain in the chest. As a result, a protective mask is required in order to function in a CS environment.

O-chlorostyrene is a raw material used by the polymer industries in polystyrene plastics, SBR, ABS and SAN resins for protective coatings (styrene-butadene latex; alkyds), styrenated polyesters, rubber-modified polystyrene copolymer resins. The chlorine atom on the styrene molecule affects the temperature properties of the plastic, making it stable at higher temperatures and having fire retardant characteristics. In the past, excessively high production costs, resulting from difficult and expensive synthesis procedures, hindered the production and marketing of o-chlorostyrene even though it possessed these desirable properties.

Ammonium sulfate, $(NH_4)_2 SO_4$, is used for fertilizers, water treatment, fermentation, fireproofing compositions, viscose rayon, tanning, and food additives. It is derived from (a) ammonical vapors from destructive distillation of coal react with sulfuric acid, followed by crystallization and drying; (b) synthetic ammonia neutralized with sulfuric acid; (c) a by-product of manufacture of caprolactam; and (d) from gypsum, by reaction with ammonia and carbon dioxide.

In accordance with the present invention CS is converted to o-chlorostyrene and ammonium sulfate by a two step chemical reaction process. The first is an acid e.g., sulfuric acid or base catalyzed hydrolysis of CS to convert it to o-chlorocinnamic acid and ammonium sulfate. The second reaction is a catalytically decarboxylate to convert the intermediate product, (o-chlorocinnamic acid) to form o-chlorostyrene.

In accordance with the present invention, two molecules of nitrogen are removed from CS to eleminate the cyanide danger. This is done by reacting water with CS to get ammonium sulfate in a sulfuric acid medium. If other acids or base are used, other end products will be obtained other than ammonium sulfate. If hydrochloric acid is used the result would be ammonium chloride, a useful chemical. Sodium hydroxide produces ammonium hydroxide, another useful chemical. If nitrous acid is used, the end product is ammonium nitrate, an explosive. Sulfuric acid is preferred because it is relatively inexpensive and the ammonium sulfate results in an effective fertilizer.

The first reaction, the sulfuric acid catalyzed hydrolysis of CS, produces o-chlorocinnamic acid. The reaction parameters, the acid concentrations, the reaction residence times, and the reaction temperatures may be varied respectively, from 40% to 80%, from 30 minutes to 10 hours, and from 90° C. A yield of 90% is obtained when CS is reacted with 70% sulfuric acid for four hours 40 minutes while the temperature is maintained at 120°–130° C. Ammonium sulfate is the by-product from this reaction.

Two carbon molecules must next be removed from the above resultant in order to obtain the desired o-chlorostyene objective. This is done by reacting the carbon molecules with water, producing two molecules of carbon dioxide, a harmless gas. After this is done, o-chlorostyrene is produced.

The second reaction, the catalytic decarboxylation reaction of o-chlorocinnamic acid, produces o-chlorostyrene and $CO_2$ gas. Two catalysts, soda lime and copper powder increase the reaction rates of decarboxylation. An average yield of about 50% may be obtained from this decarboxylation reaction. The crude product from this reaction can be distilled at a reduced pressure (15 torr) and at a temperature of 76° C. to obtain a 37% yield of light yellow product, o-chlorostyrene of 91% purity. The range of reaction temperature is from 270° C. to 460° C. The residue (a black tar) from the decarboxylation reaction is a polymeric material which has not been recovered or identified at this time. This proposed process converts bulk CS to valuable products, a o-chlorocinnamic acid (an intermediate product), o-chlorostyrene (the final product), and ammonium sulfate.

Thus the overall reaction is the addition of four moles of $H_2O$ per mole of CS, and one mole of sulfuric acid, produces two moles of $CO_2$ gas, one mole of ammonium sulfate, and one mole of o-chlorostyrene.

BRIEF DESCRIPTION OF DRAWINGS

FIG. 1 illustrates the chemical structure of CS (o-Chlorobenzalmalononitrile),

FIG. 2 illustrates the acid catalyzed hydrolysis reaction of bulk CS when sulfuric acid is used as a catalyst, FIG. 3 illustrates the final products from the reaction shown in FIG. 2, FIG. 4 illustrates a second reaction, the decarboxylation of o-chlorocinnamic acid to o-chlorostyrene, FIG. 5 illustrates the overall chemical reaction, FIG. 6 is a CS conversion flow chart, and FIG. 7 illustrates a preferred CS conversion plant arrangement.

DETAILED DESCRIPTION OF PREFERRED EMBODIMENT OF INVENTION

Reference is now made of FIG. 1 which shows the chemical structure of CS (tear gas). This chemical compound contains two nitrile functional groups at the second position of the vinylic end of the molecule. Removal of these two nitrile functional groups effects the chemical conversion of bulk CS to o-chlorostyrene. The overall process involves two chemical reactions in series requiring several steps. The first reaction is an acid or base catalyzed hydrolysis of CS (adding acid and water as catalysts) to convert it to o-chlorocinnamic acid. The second reaction is the decarboxylation (removal of carbon dioxide) of this intermediate product to give o-chlorostyrene.

When sulfuric acid is used as a catalyst in the hydrolysis reaction of bulk CS, the initial product is the diamide formed by addition of $H_2O$ to the nitrile groups as illustrated in FIG. 2. Since amides are also hydrolyzed by acid, the free acid (o-chlorocinnamic acid), ammonium sulfate, and $CO_2$ gas are the final products from this reaction, as illustrated in FIG. 3.

The second reaction, the decarboxylation of o-chlorocinnamic acid to o-chlorostyrene is facilitated by the nature of the resonance structures of the alpha, beta-unsaturated free acid, and the ability of the ionic o-chlorocinnamic acid to disperse electron density over the entire structure of the mole. This decarboxylation reaction is illustrated in FIG. 4.

The overall reaction is illustrated in FIG. 5, showing that one mole of CS is reacted with four moles of water and one mole of sulphuric acid, resulting in producing one mole of o-chlorostyrene, one mole of ammonium sulfate and two moles of carbon dioxide.

The flow chart for the CS conversion is illustrated in FIG. 6. Here is shown a glove box 10 into which a container of CS is inserted for opening. CS is a powder form and must be kept in an enclosure to avoid adverse effect on the operator or surrounding atmosphere. Tank 12 contains water and sulfuric acid which is sprayed onto the CS in the glove box 10. From the glove box the CS is pumped into a holding/mixing tank 14 where it is heated. From tank 14 the mixture is pumped into a reactor 16 where heat (approximately 125° C.) and agitation is used to expell $CO_2$ to atmosphere. From reactor 16 the reacted material is pumped to a dilutor 18 where water from tank 20 is added. Holding tank 22 receives the diluted mixture until it is pumped into centrifuge 24. Liquid from the centrifuge 24 is pumped into an ammonolyses tank 26 where ammonia from tank 28 is added and mixed until the acid is neutralized. From the ammonolyses tank 26 the liquid is pumped into evaporator tank 30 where it is heated under a vacuum to boil off water which is returned to tank 20. The resultant ammonium sulfate is then stored in storage tank 32, where it is available for packaging and subsequent use. This portion of the flow chart depicts a continous flow process.

To remove the 10% impurity, (as indicated earlier a 90% yield occurs in the first reaction) the following purification process is performed. The heavier wet mass is separated from the liquid in centrifuge 24. It is pumped into a basifier tank 34 and treated with a dilute sodium hydroxide solution from sodium hydroxide storage tank 36, dissolving the crude product into a liquid. This liquid is pumped back into centrifuge 24, separating the dissolved liquid from the solid impurity which is recycled back to glove box 10 for reprocessing.

The liquid from cetrifuge 24 is pumped into neutralizer tank 38, and treated with a dilute hydrochloric acid solution from hydrochloric acid storage tank 40, inducing the intermediate product (o-chlorocinnamic acid) to precipitate into a solid. This mixture of solid and liquid is again pumped back to centrifuge 24 where it is again separated into solid and liquid. The liquid, which contains sodium chloride (salt), is pumped into salt storage tank 42 where it is checked for toxic materials before sewage disposal. The solid from centrifuge 24 is placed in a dryer where it is heated and dried and deposited in a hopper 46.

The second reaction occurs in reactor 48 where it is heated in the presence of soda lime and copper powder at 270° C., and more $CO_2$ is vented to atmosphere. Thereafter the residue gas is condensed to o-chlorostyrene in storage tank 52. This portion of the flow chart depicts a batch process, as opposed to the earlier described continous flow process.

FIG. 7 illustrates a typical pilot plant arrangement with equipment numbered to correspond to that shown in FIG. 6. Hence, further description is not deemed to be necessary.

The invention in its broader aspects is not limited to the specific combinations, improvements and instrumentalities describe departures may be made therefrom within the scope of the accompany claims without departing from the principles of the invention and without sacrificing its chief advantages.

What is claimed is:

1. Method for converting O-Chlorobenzalmalononitrile to O-Chlorostyrene, which comprises subjecting the O-Chlorobenzalmalononitrile to hydrolysis to produce O-Chlorocinnamic acid and subjecting the O-Chlorocinnamic acid to decarboxylation to produce O-Chlorostyrene.

2. The method of claim 1, wherein the hydrolysis is catalyzed with an acid.

3. The method of claim 2, wherein the acid is sulfuric acid and ammonium sulfate is produced.

4. The method of claim 1, wherein the hydrolysis is catalyzed with a base.

5. The method of claim 1, wherein the decarboxylation is carried out in the presence of a catalyst.

6. The method of claim 5, wherein the catalyst is a mixture of NaOH, CaO and Cu.

7. The method of claim 6, wherein the decarboxylation is carried out at a temperature ranging from about 270° C. to 460° C.

* * * * *